US006791682B2

(12) United States Patent
Kobayashi

(10) Patent No.: US 6,791,682 B2
(45) Date of Patent: Sep. 14, 2004

(54) APPARATUS FOR INSPECTING DISPLAY PANEL AND METHOD FOR INSPECTING THE SAME

(75) Inventor: Shigetaka Kobayashi, Yasu-gun (JP)

(73) Assignee: International Business Machines Corporation, Armonk, NY (US)

( * ) Notice: Subject to any disclaimer, the term of this patent is extended or adjusted under 35 U.S.C. 154(b) by 253 days.

(21) Appl. No.: 09/683,701

(22) Filed: Feb. 5, 2002

(65) Prior Publication Data

US 2002/0105638 A1 Aug. 8, 2002

(30) Foreign Application Priority Data

Feb. 6, 2001 (JP) ........................................ 2001-029306

(51) Int. Cl.[7] .............................................. G01N 21/896
(52) U.S. Cl. .................... 356/239.1; 356/239.2
(58) Field of Search ................. 356/237.1, 237.2–237.5, 356/239.1, 239.2, 432–436

(56) References Cited

U.S. PATENT DOCUMENTS 4,095,898 A * 6/1978 Fulwyler .................... 356/338
4,622,584 A * 11/1986 Nagasaki et al. ............. 348/69
6,064,477 A * 5/2000 Matsumoto et al. ...... 356/237.2

FOREIGN PATENT DOCUMENTS

| JP | 04248435 A | 3/1992 | .......... G01M/11/00 |
| JP | 07325009 A | 12/1995 | .......... G01M/11/00 |

* cited by examiner

Primary Examiner—Richard A. Rosenberger
Assistant Examiner—Vincent P. Barth
(74) Attorney, Agent, or Firm—Anthony J. Canale

(57) ABSTRACT

A lighting inspection apparatus is provided which uses a small backlight comprised of a dimmer plate and a xenon lamp or a fluorescent lamp that miniaturizes the inspection apparatus for a display panel. An inspection method is described for a display panel, which uses a dimmer plate autonomously adjusting light. The apparatus for inspecting a display panel includes: a support structure disposing thereon a display panel to be inspected; a light source; and a dimmer plate with a characteristic modulating a light transmission characteristic in accordance with an intensity of light incident thereonto, the dimmer plate being disposed between the support structure and the light source, wherein light emitted from the light source is made to transmit through the dimmer plate, then made incident onto the display panel disposed on the support structure.

8 Claims, 6 Drawing Sheets

100

APPARATUS FOR INSPECTING DISPLAY PANEL AND METHOD FOR INSPECTING THE SAME

BACKGROUND OF THE INVENTION

The present invention relates to an apparatus for inspecting a liquid crystal display panel mainly for use in a manufacturing process for a liquid crystal display device.

BACKGROUND OF THE INVENTION

In the manufacturing process for a liquid crystal display device, before driver ICs are mounted onto a liquid crystal display panel, the liquid crystal display panel is inspected for pixel defects, insufficient or uneven color, luminance and the like by lighting a liquid crystal panel substrate with liquid crystal sealed therein. In an inspection apparatus for use in the inspection, light from a light source is irradiated onto the liquid crystal display panel to inspect a transmission characteristic thereof. Such inspection is called a lighting inspection, a cell inspection or a panel inspection, which is called a lighting inspection hereinbelow.

The foregoing lighting inspection is a visual inspection, an automatic inspection using a measuring apparatus and the like, which are common in that the light from the light source is irradiated onto the liquid crystal display panel to inspect the transmission characteristic thereof.

A lighting inspection apparatus used for a conventional lighting inspection is described, for example, in the gazette of Japanese Patent Laid-Open No. Hei 4 (1992)-248435 or the gazette of Japanese Patent Laid-Open No. Hei 7 (1995)-325009. Such a conventional lighting inspection apparatus is used for performing an inspection by use of a light source equivalent to a backlight of a usual liquid crystal display device. For the backlight of the inspection apparatus, a xenon lamp or a fluorescent lamp has been used. Advantages of the xenon lamp are that the luminance is even and high, stability is high, a size is small and so on. Conversely, disadvantages thereof are that lifetime is short and costs of a control power source and of the same lamp are high. Meanwhile, for the fluorescent lamp, a straight fluorescent lamp has been used. As a structural nature thereof, light from both ends of the fluorescent lamp is dark. In this case, in order to prevent regions of the liquid crystal display panel from being darkened, onto which the light from the both ends is irradiated, a fluorescent tube longer than a size of the panel to be inspected must be used, thus an optical system of the inspection apparatus has been enlarged, leading to enlargement of the inspection apparatus itself.

BRIEF SUMMARY OF THE INVENTION

As described above, for the backlight of the lighting inspection apparatus, the xenon lamp or the fluorescent lamp has been used. In the case of using the xenon lamp, there has been a problem that a cost for common use is high though the performance is high. In the case of using a fluorescent lamp, there has been a problem that the inspection apparatus is enlarged.

The present invention was made with the foregoing problems in mind. A first object of the present invention is to realize an inspection apparatus using a small backlight constituted of a dimmer plate as well as a fluorescent lamp, thus to miniaturize the inspection apparatus for a display panel. A second object of the present invention is to propose an inspection method for a display panel, which uses a dimmer plate autonomously adjusting light.

In order to achieve the foregoing objects, according to a first aspect of the present invention, there is provided an apparatus for inspecting a display panel, comprising: a support structure disposing thereon a display panel to be inspected;

a light source; and a dimmer plate with a characteristic modulating a light transmission characteristic in accordance with an intensity of light incident thereonto, the dimmer plate being disposed between the support structure and the light source, wherein light emitted from the light source is made to transmit through the dimmer plate, then made incident onto the display panel disposed on the support structure.

In order to simplify a structure of the apparatus, a second aspect of the present invention is characterized in that, in a constitution of the first aspect, the dimmer plate modulates the light transmission characteristic in accordance with an intensity of an ultraviolet ray incident thereonto and has a reversible photochromic property.

In order to miniaturize the apparatus, a third aspect of the present invention is characterized in that, in the constitution of the first aspect, a fluorescent light emitting tube made of a bent glass tube is provided as the light source.

In order to make even brightness on a surface to be inspected, a fourth aspect of the present invention is characterized in that, in the constitution of the first aspect, a light diffusion plate is disposed between the dimmer plate and the display panel to be inspected.

According to a fifth aspect of the present invention, there is provided a method for inspecting a display panel, said method comprising the steps of:

disposing a display panel to be inspected on a support structure; emitting light from a light source;

making the light emitted from said light source incident onto a dimmer plate, and modulating a light transmission characteristic in accordance with an intensity of the incident light, thus controlling a quantity of light transmitted through the dimmer plate; and making the transmitted light incident onto the display panel to be inspected, the transmitted light having the controlled quantity.

A sixth aspect of the present invention, which relates to an optical route, is characterized in that, in the method of the fifth aspect, the transmitted light having the controlled quantity is diffused, and the diffused light is made incident onto the display panel to be inspected.

A seventh aspect of the present invention, which relates to a method for utilizing a dimmer plate, is characterized in that, in the method of the fifth aspect, the step of controlling a quantity of transmitted light modulates the light transmission characteristic in accordance with an intensity of an incident ultraviolet ray and utilizes a reversible photochromic property.

An eighth aspect of the present invention, which relates to a concrete inspection method, in the method of the fifth aspect, further comprises the step of: comparing a transmission intensity of light detected after being transmitted through the display panel and a predetermined transmission intensity of light in a standard sample with each other.

BRIEF DESCRIPTION OF THE SEVERAL VIEWS OF THE DRAWINGS

For a more complete understanding of the present invention and the advantages thereof, reference is now made to the following description taken in conjunction with the accompanying drawings.

FIG. 5A shows measurement points; and FIG. 5B shows luminance distributions on the respective measurement points in the following cases made for achieving the evenness of the luminance, in which a line A shows a luminance distribution in the case of using two fluorescent lamps of an electric light bulb type, two diffusion plates, two Fresnel plates and a white acrylic plate with a thickness of 3 mm; a line B shows a luminance distribution in the case of using a straight fluorescent lamp and a white acrylic plate with a thickness of 3 mm; a line C shows a luminance distribution in the case of using a xenon lamp and a white acrylic plate with a thickness of 3 mm; and a line D shows a luminance distribution in the case of using a backlight for use in a liquid crystal display product.

DETAILED DESCRIPTION OF THE INVENTION

Hereinbelow, description will be made in detail for embodiments of the present invention with reference to the accompanying drawings. First, description will be for a basic principle constituting the present invention.

Figure 2:
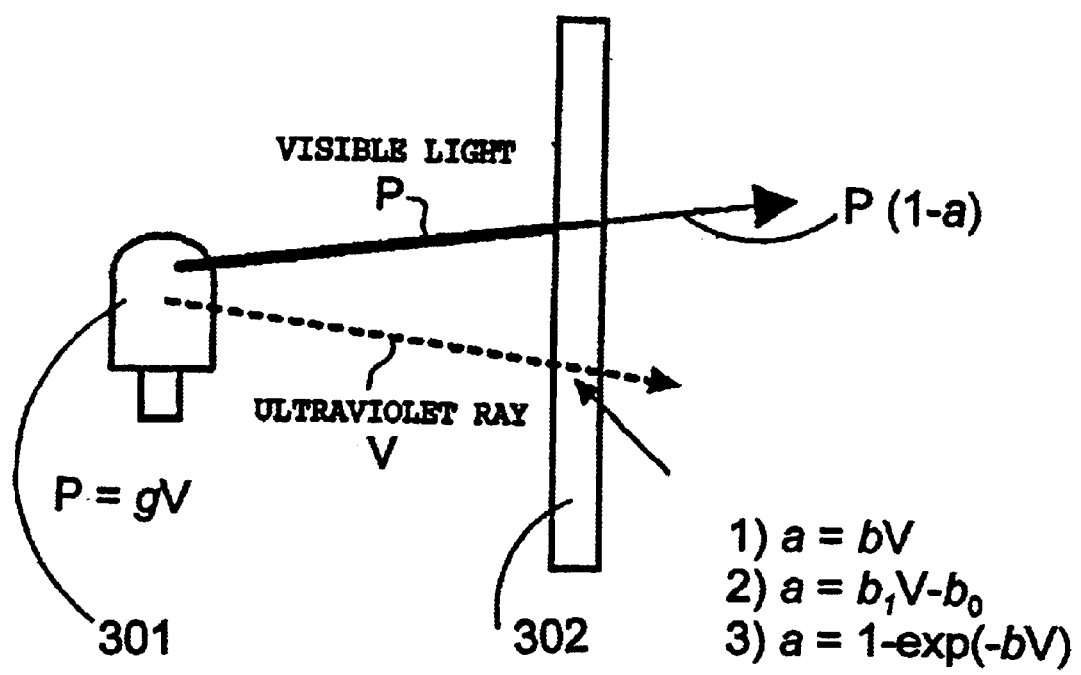
FIG. 2 is a conceptional view showing an effect of a dimmer plate.

FIG. 2 is a schematic view for explaining the basic principle of the present invention. It is assumed that visible light with an intensity P and an ultraviolet ray with an intensity V are emitted from a light source 301. Since the intensity of the visible light and the intensity of the ultraviolet ray are generally proportional to each other, a relationship therebetween can be represented as:

P=gV, where g is a proportionality coefficient. It is assumed that, generally, when the visible light is transmitted through a dimmer plate 302, the visible light is attenuated by Pa and the rest P (1−a) is transmitted therethrough, where a is an absorptivity. Moreover, it is assumed that the dimmer plate 302 is colored only by the ultraviolet ray, thereby the absorptivity a is varied in proportion to the intensity V of the ultraviolet ray. Specifically, a relation of: a=bV is established, where b is a proportionality coefficient.

Under the situation as described above, the intensity of the light transmitted through the dimmer plate 302 is represented as: P(1−a), which is equal to gV(1−bV). It is readily reached that, in this function, a maximum value is obtained when V=1/(2b) and a V-dependance (hence, a P-dependance) is minimum in the vicinity thereof. Moreover, the light intensity at this time is P/2, which is half the intensity of the initial light intensity P.

As described above, a transmission characteristic of the dimmer plate is adjusted so that the intensity of the transmitted light can be a half of the initial one, thus the intensity of the light outputted from the dimmer plate can be stabilized. Moreover, it can be readily understood that, when a variance of the light intensity exists depending on a position in the dimmer plate, the variance is reduced.

Moreover, it is assumed that the dimmer plate 302 is colored only by the ultraviolet ray, there is a threshold in the intensity of the light for such coloring, and the dimmer plate is not colored by an ultraviolet ray with an intensity equal to the threshold or less. It is assumed that the absorptivity a has a linear relationship with the intensity V of the ultraviolet ray. The relationship is represented as: $a=b_1V-b_0$. Specifically, when $V>b_0/b_1$, $a=b_1V-b_0$. And when $V<b_0/b_1$, $a=0$. Here, $b_0$ and $b_1$ are proportionality coefficients. In this case, by a discussion similar to the above, the intensity of the light transmitted through the dimmer plate is represented as: P(1−a), which is equal to $gV(1-(b_1V-b_0))$. It is readily reached that this function takes the maximum value when $V=(1+b_0)/(2b_1)$, and the V-dependance (hence, the P-dependance) is minimum in the vicinity thereof. Moreover, the intensity of the light at this time is $P(1+b_0)/2$, which is equal to a half of the initial one or more. Therefore, the intensity of the light can be increased more than the foregoing case.

It is assumed that the dimmer plate 302 is colored only by the ultraviolet ray. When the absorptivity a of the visible light depends on the intensity V of the ultraviolet ray non-linearly in such a manner that a=1−exp(−bV) is established (b is constant), and when the transmittance of the visible light is represented as (1−a), then by the discussion similar to the above, the intensity of the light transmitted through the dimmer plate is represented as: P(1−a), which is equal to gV(exp(−bV)). It is readily reached that the function takes the maximum value when V=1/b and the V-dependance (hence, the P-dependance) is minimum in the vicinity thereof. What is also understood is that the intensity of the light at this time is represented as: P/e when e is set as a base of a natural logarithm and may be adjusted so as to be 1/2.7 of the initial intensity.

Even if a and V have a more complicated relation, when the intensity P(1−a) of light transmitted through the dimmer plate is regarded as a function of the intensity of the ultraviolet ray of the light source or the intensity of the visible light thereto, it is apparent that the variance of the intensity of the light can be leveled at an operating point of the light source, where the intensity P(1−a) of the light transmitted through the dimmer plate is not increased even when the intensity of the ultraviolet ray of the light source is increased. From the above, it is desirable that the operating point be adjusted to be at a position in the dimmer plate, which indicates an approximately average intensity of the light. The operating point as described above can be realized by a method such as adjusting the intensity of the light of the light source, selecting a dimmer plate having a suitable photochromic property and adjusting the intensity of the light incident onto the dimmer plate.

Moreover, though the photochromic property that the dimmer plate 302 is colored only by the ultraviolet ray has been assumed in the above description, any trouble is not particularly caused even if the dimmer plate is colored by the visible light or light with a wavelength longer than the visible light.

Figure 1:
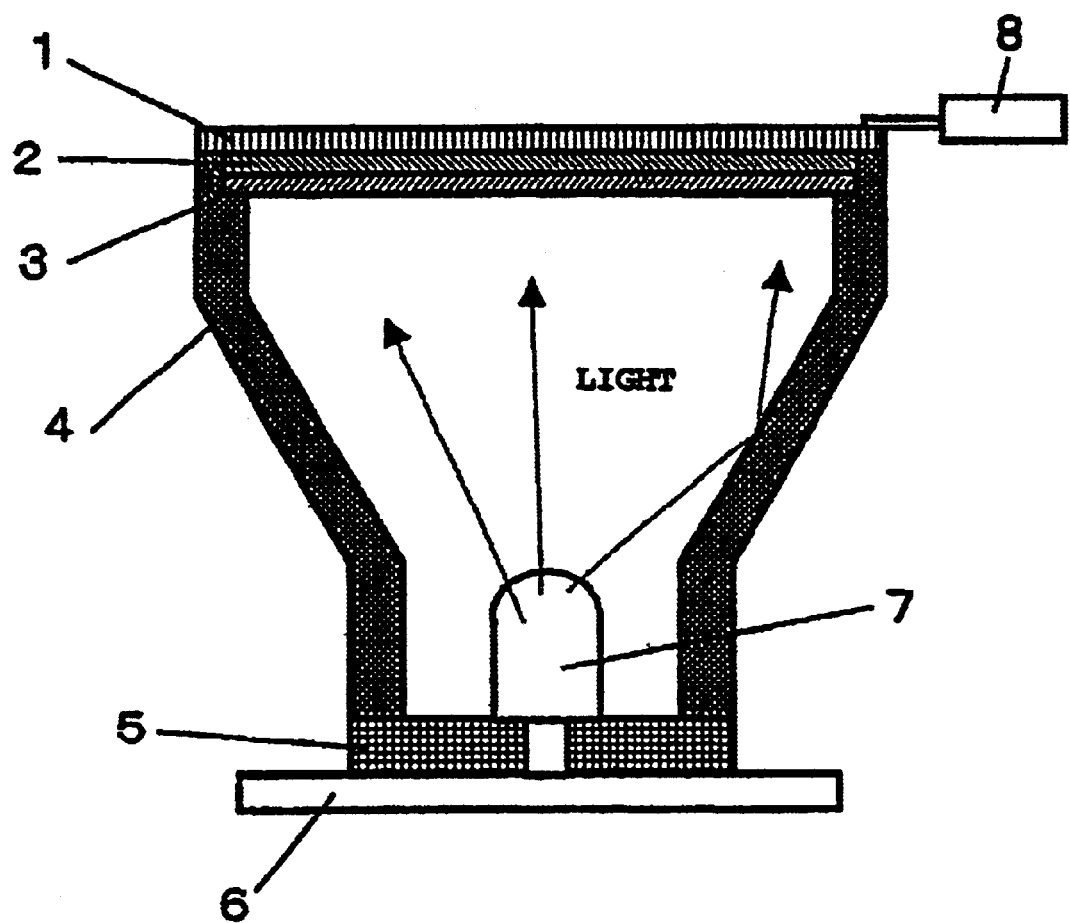
FIG. 1 is a sectional view schematically showing a backlight.

Next, description will be made for a first embodiment with reference to FIG. 1. FIG. 1 is a sectional view showing a backlight 100 of the inspection apparatus for a display panel of the present invention. Here, a liquid crystal panel 1 to be inspected is placed on the uppermost portion of the backlight unit 100 as shown in FIG. 1. A white acrylic light diffusion plate 2 is placed under the liquid crystal panel 1. On the entire surface of the diffusion plate 2, a diffusion sheet is adhered so as to prevent reflection of light or unevenness due to interference. Alternatively, the surface of the diffusion plate 2 may be subjected, for example, to a satin finish or the like.

A dimmer plate 3 is provided between a light source 7 and the white acrylic diffusion plate 2. In order to eliminate, as much as possible, change in the relation between the intensities of the ultraviolet ray and the visible light from the light source 7 even after the inspection apparatus is used for a long period of time, it is desirable that provision of optical elements between the dimmer plate 3 and the light source 7 be eliminated as much as possible. As such change, for example, change in ratio of the intensities of the ultraviolet ray and the visible light for each spectrum is mentioned. Therefore, for example, disposition described as above is more desirable than disposition in which the white acrylic diffusion plate 2 is provided between the dimmer plate 3 and the light source 7. The dimmer plate 3 is a light attenuation plate having a reversible photochromic property, which is already available in the market. Here, an advantage that the photochromic property is reversible is in that the dimmer plate 3 can cope with lowering in luminance of the light source. Moreover, in order to eliminate a necessity of tone correction by the other apparatus, it is desirable that a tone of the dimmer plate 3 be set between white and black. Furthermore, it is desirable that a distance between the dimmer plate 3 and the light source 7 be adjusted in response to a necessary intensity of the ultraviolet ray. With regard to a shape of the dimmer plate 3, a planar shape is desirable since it is easy to be prepared. However, a convex lens, a concave lens or a shape obtained by combining these lenses may be provided on the surface of the dimmer plate 3 according to needs, thereby contributing the diffusion of light. Such lenses may be provided for each light source, or a large number of microlenses may be provided. Furthermore, the diffusion of the light, provision of a disordered uneven pattern can be also effective.

The convex lens, the concave lens or the shape obtained by combining these lenses, alternatively the microlenses or the disordered uneven pattern, which are described as above, may not be provided on the dimmer plate but may be provided on a transparent planar matter, which is separately prepared. Thus, the dimmer plate is shaped to be like a planar plate, a convex lens or a concave lens as a whole. Thereby, the cost of the dimmer plate can be reduced.

As the dimmer plate 3, a light attenuation plate having an irreversible photochromic property can be used. In this case, an ultraviolet ray is previously irradiated onto the attenuation plate by an apparatus of the same type as the above-described one, which is equipped with a source of an intense ultraviolet ray, and the attenuation plate is colored by photochromism, thus a function similar to the above can be imparted thereto. However, in this method, there are disadvantages that the transmission characteristic of the dimmer plate tends to be changed for a long period of time and it is difficult to cope with the lowering of luminance in the light source.

In FIG. 1, the liquid crystal panel 1, the white acrylic diffusion plate 2 and the dimmer plate 3 are in close contact from one to another. However, it is possible to provide the liquid crystal panel 1, the diffusion plate 2 and the dimmer plate 3, each being spaced from the other. Particularly, in the case where a temperature distribution is generated in the liquid crystal panel 1 due to heat transfer, the liquid crystal panel 1, the diffusion plate 2 and the dimmer plate 3 are provided, each being sufficiently spaced from the other, and air thereamong is diffused or exhausted according to needs, thus the generation of the temperature distribution in the liquid crystal panel 1 can be avoided.

An inner surface of a cell stage 4 is subjected to a satin finish by sandblast in order to diffuse light while maintaining high reflectivity of the light. Moreover, since a shape of the inner surface affects the illuminance on the liquid crystal panel, the shape must be designed so that the illuminance on the liquid crystal panel can be made even. The cell stage 4 is linked with a cell stage base 5, which is fixed to a frame of the inspection apparatus for a display panel through a cell stage attachment base 6.

The light source 7 is single or plural according to needs and is fixed to the cell stage base 5. As the light source 7, a commercially available fluorescent lamp of an electric light bulb type can be used, the fluorescent lamp including a bent fluorescent tube, in order to miniaturize the inspection apparatus for a display panel. From the fluorescent lamp, an ultraviolet ray as a spectrum of mercury and visible light obtained by converting the ultraviolet ray by a fluorescent material are emitted. An effect by use of the fluorescent lamp is that the apparatus can be miniaturized as described above. By realizing a small-sized inspection apparatus, a manufacturing cost of the apparatus itself can be reduced. In the case where the inspection is disposed in a clean room, a footprint of the apparatus is decreased, thus making it possible to reduce an accompanying cost. For the light source 7, a linear-shaped fluorescent lamp and a fluorescent lamp of the foregoing electric light bulb type can be also used in combination. Fluorescent tubes of these fluorescent lamps have different degradation characteristics from each other due to different shapes thereof or the like, and luminance distributions thereof are varied with time. However, such luminance distributions are relieved to a great extent by use of the dimmer plate 3. Moreover, it is apparent that a similar function can be exerted also in such a manner that an ultraviolet lamp without a fluorescent material is used as the light source 7, and that a fluorescent plate coated with the fluorescent material is provided between the dimmer plate 3 and the light source 7. Furthermore, since the light source 7 generates heat, it may cause a temperature distribution on the dimmer plate 3 in some cases. In the case where a distribution is caused in the photochromic property due to the temperature distribution, it is desirable that air in contact with the light source be diffused or exhausted.

In order to inspect a display state of the pattern by applying electric signals to the liquid crystal panel 1, electric contacts are provided onto drawing terminals of the liquid crystal panel 1 by use of probe needles or flat board probes (FBP) 8. Such contacts are performed on a side in an X-direction of the liquid crystal panel 1 and a side in a Y-direction thereof. However, since driver ICs are not attached to the liquid crystal panel 1 at this inspection step, the number of contacts becomes a value corresponding to that of the foregoing drawing terminals or a value obtained by dividing the number of drawing terminals into some blocks. Display of a specified pattern or display without a pattern is performed by applying predetermined signals to these terminals. The luminance or a pattern abnormality on the display surface is visually inspected or automatically inspected by use of a color meter or a luminance meter.

In such an inspection, particularly in the case of performing the visual inspection, it is desirable that the inspected panel be compared with a standard sample previously prepared. Multi-point measurement is performed in the case of the automatic inspection. In this case, measured values of the case where the liquid crystal panel 1 is not placed should be previously prepared, and it is desirable to compare the measured values with measured values of the case where the liquid crystal panel 1 is placed.

Figure 3:
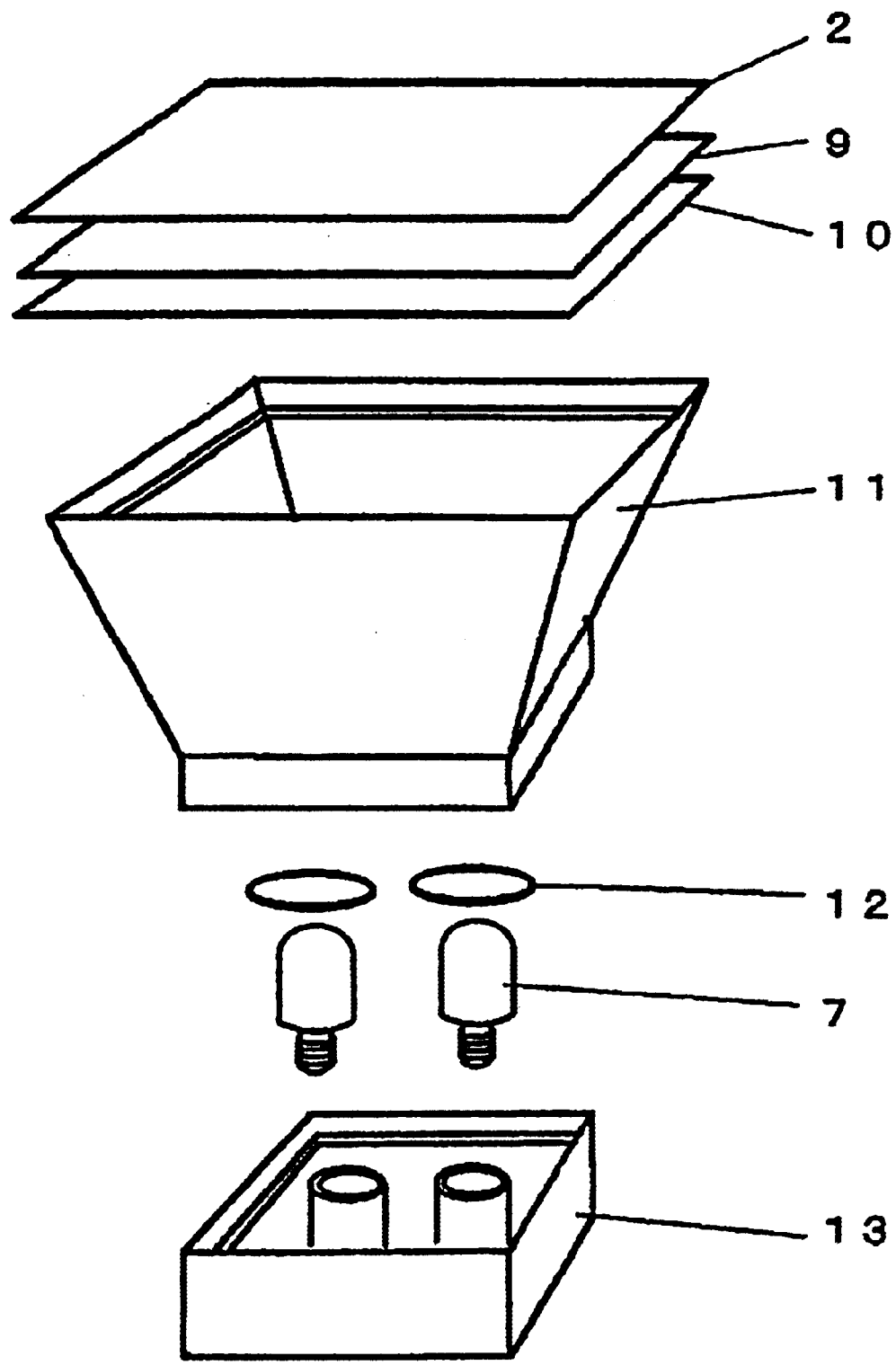
FIG. 3 is a view showing an assembly order of a backlight for an inspection apparatus for a display panel in accordance with the present invention.

Next, description will be made for a second embodiment with reference to a schematic view of FIG. 3. FIG. 3 shows an assembly order of a backlight 101 for the inspection apparatus for a display panel. The backlight 101 is comprised of: the light diffusion plate 2; a diffusion sheet 9; a mirror film 10; a reflection filter 11; dimmer lenses 12; fluorescent lamps 7 of the electric light bulb type; and a socket 13 for the fluorescent lamps. These parts are assembled to make a constitution similar to that shown in the sectional view of FIG. 1. Here, a function of the mirror film 10 is to promote the diffusion of light and enhance the evenness of the illuminance on the liquid crystal panel surface. The reflection filter 11 is processed to remove an infrared ray or a near-infrared ray. The dimmer lenses 12 are convex lenses made of a with a reversible photochromic property. These lenses are fixed to a light shielding matter and used as windows transmitting light therethrough.

Figure 4:
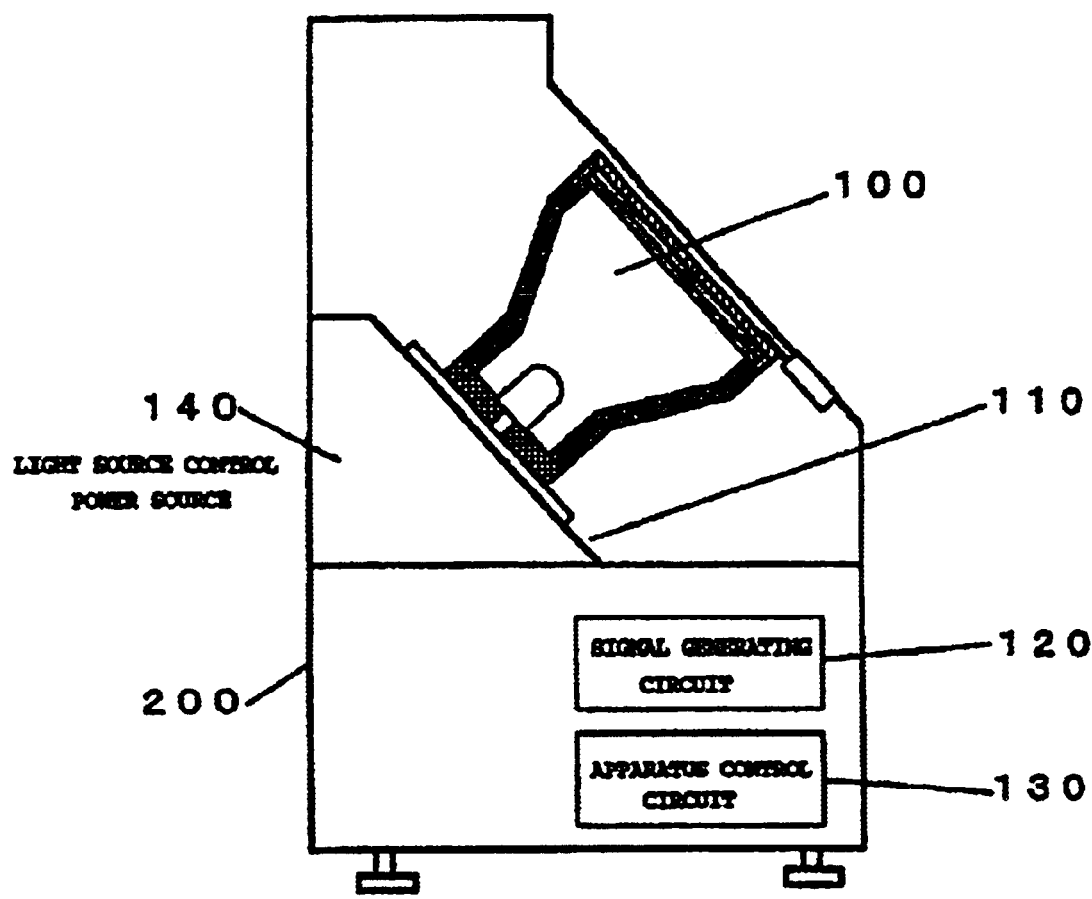
FIG. 4 is a sectional side view of the inspection apparatus for a display panel.

FIG. 4 is a sectional side view of an inspection apparatus 200 for a display panel of the present invention. Besides the foregoing backlight 100, the inspection apparatus 200 for a display panel is constituted of: a cell stage fixing frame 110; a signal generating circuit 120 for a liquid crystal panel; an apparatus control circuit 130; and a lamp control power source 140.

Figures 5A, 5B:
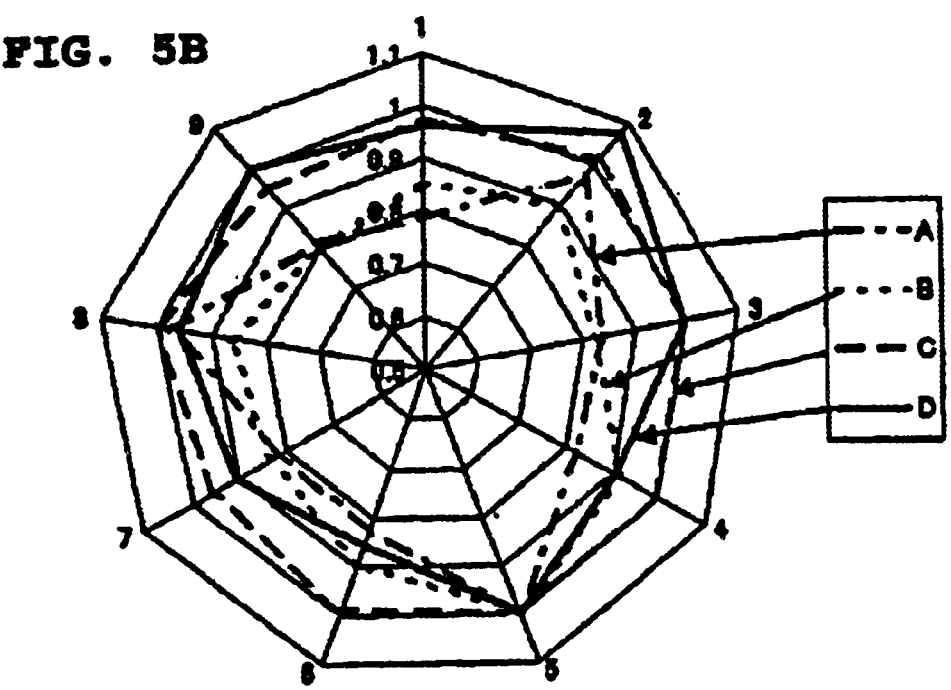
FIGS. 5A and 5B are a table and a graph showing luminance distributions of the backlight on a surface onto which the liquid crystal panel is mounted.

Next, description will be made for an improvement effect for the luminance of the backlight, which is brought by the constitution of the present invention. In order to see the distribution of the luminance of the backlight on the surface, onto which the liquid crystal panel is mounted, as shown in FIG. 5A, the surface is divided into nine blocks (3×3), and results obtained by measuring the luminance in the blocks by use of the luminance meter are shown in FIG. 5B. In FIG. 5B, distributions standardized by the luminance on a spot 5 as a center block on the surface are shown. Here, there are shown luminance distributions in the following cases, which were made for achieving the evenness of the luminance. Specifically, a line A shows a luminance distribution in the case of using two fluorescent lamps of the electric light bulb type, two diffusion plates, two Fresnel plates and a white acrylic plate with a thickness of 3 mm. A line B shows a luminance distribution in the case of using a straight fluorescent lamp and a white acrylic plate with a thickness of 3 mm. A line C shows a luminance distribution in the case of using a xenon lamp and a white acrylic plate with a thickness of 3 mm. And a line D shows a luminance distribution in the case of using a backlight for use in a liquid crystal display product. From the graph of FIG. 5B, it is understood that the luminance distribution is the most uneven in the case of using the fluorescent lamp of the electric light bulb type, which is shown by the line A.

Figure 6:
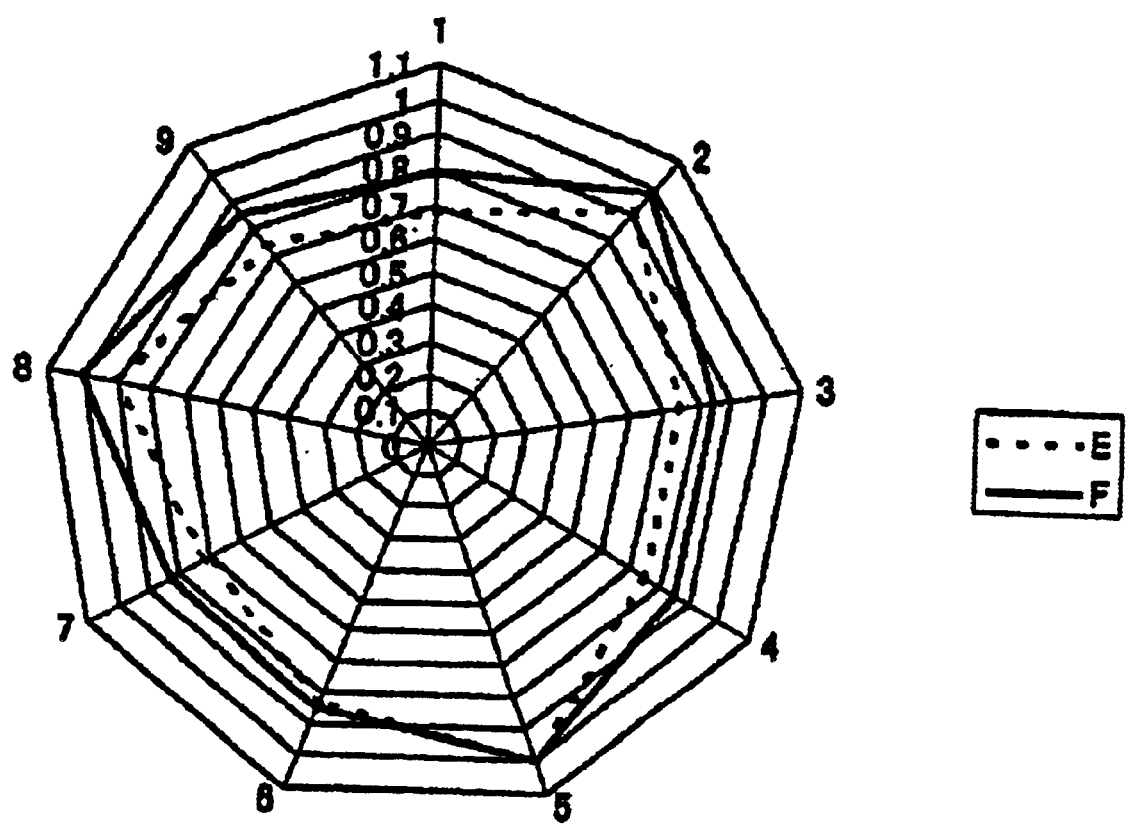
FIG. 6 is a graph showing a comparison result of a luminance distribution in the case of using a dimmer plate and that in the case of not using a dimmer plate in an inspection apparatus using the fluorescent lamp of the electric light bulb type, in which a line E shows a luminance distribution in the case of not using the dimmer plate in an inspection apparatus having a diffusion plate adhered onto an inner surface of a cell stage, and a line F shows a luminance distribution in the case of using a dimmer lens in an inspection apparatus having a diffusion plate adhered onto the inner surface of the cell stage similarly to the case in the line E.

In order to see a correction effect of the luminance by the dimmer plate in the inspection apparatus using the fluorescent lamp of the electric light bulb type, as shown in FIG. 6, a luminance distribution in the case of using the dimmer plate and a luminance distribution in the case of not using the dimmer plate were compared with each other. In FIG. 6, a line E shows a luminance distribution in the case of not using the dimmer plate in an inspection apparatus having a diffusion plate adhered onto the inner surface of the cell stage. And, a line F shows a luminance distribution in the case of using a dimmer lens in an inspection apparatus having a diffusion plate adhered onto the inner surface of the cell stage similarly to the case in the line E. As understood from the graph, the luminance distribution is improved by about 10% in a peripheral portion of the surface.

As described above, unevenness in luminance, which is caused by use of the small-sized fluorescent lamp of the electric light bulb type as a light source, is corrected by use of the dimmer plate or the dimmer lens using a photochromic effect, thus constituting the present invention. Accordingly, the unevenness in luminance is automatically corrected, and the luminance distribution is improved by about 10%. And, the inspection apparatus for a display panel is obtained, which is smaller than the conventional one while having the performance approximately equal to the conventional one.

Although the preferred embodiments of the present invention have been described in detail, it should be understood that various changes, substitutions and alterations can be made therein without departing from spirit and scope of the inventions as defined by the appended claims.

What is claimed is:

1. An apparatus for inspecting a display panel, comprising:
    a support structure on which a display panel to be inspected is disposed;
    a light source; and
    a dimmer plate which modulates a light transmission characteristic in accordance with an intensity of light incident onto said dimmer plate; said dimmer plate being disposed between said support structure and said light source,
    wherein light emitted from said light source is transmitted through said dimmer plate, then incident onto the display panel disposed on said support structure.

2. The apparatus according to claim 1, wherein said dimmer plate modulates the light transmission characteristic in accordance with an intensity of an ultraviolet ray incident onto said dimmer plate and has a reversible photochromic property.

3. The apparatus according to claim 1, wherein said light source comprises a fluorescent light emitting tube made of a bent glass tube.

4. The apparatus according to claim 1, wherein a light diffusion plate is disposed between said dimmer plate and the display panel to be inspected.

5. A method for inspecting a display panel, said method comprising the steps of:
    disposing a display panel to be inspected onto a support structure;
    emitting light from a light source;
    receiving the light emitted from said light source, and controlling a quantity of transmitted light in accordance with an intensity of the incident light; and
    making said transmitted light incident onto said display panel to be inspected, said transmitted light having the controlled quantity.

6. The method according to claim 5, wherein said transmitted light having the controlled quantity is diffused, and the diffused light is made incident onto the display panel to be inspected.

7. The method according to claim 5, wherein said step of controlling a quantity of transmitted light controls the quantity in accordance with an intensity of an incident ultraviolet ray by utilizing a reversible photochromic property.

8. The method according to claim 5, further comprising the step of: comparing a transmission intensity of light detected after being transmitted through the display panel and a predetermined transmission intensity of light in a standard sample with each other.

* * * * *